United States Patent
Inoue

(10) Patent No.: US 7,492,936 B2
(45) Date of Patent: Feb. 17, 2009

(54) RADIOGRAPHIC IMAGE CAPTURING APPARATUS

(75) Inventor: Hitoshi Inoue, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 820 days.

(21) Appl. No.: 11/111,901

(22) Filed: Apr. 22, 2005

(65) Prior Publication Data

US 2005/0244044 A1 Nov. 3, 2005

(30) Foreign Application Priority Data

Apr. 30, 2004 (JP) ............................ 2004-136018

(51) Int. Cl.
G06K 9/00 (2006.01)
(52) U.S. Cl. .................................... 382/128
(58) Field of Classification Search ................. 382/128, 382/132
See application file for complete search history.

(56) References Cited

U.S. PATENT DOCUMENTS

| 5,359,513 | A | * | 10/1994 | Kano et al. ................. 382/128 |
| 5,570,430 | A | * | 10/1996 | Sheehan et al. ............. 382/128 |
| 6,067,373 | A | * | 5/2000 | Ishida et al. ................ 382/130 |
| 6,343,143 | B1 | * | 1/2002 | Guillemaud et al. ........ 382/130 |
| 6,594,378 | B1 | * | 7/2003 | Li et al. ...................... 382/128 |
| 2003/0016854 | A1 | | 1/2003 | Inoue et al. ................. 382/132 |
| 2004/0028286 | A1 | | 2/2004 | Saigusa et al. ............. 382/264 |
| 2005/0243967 | A1 | | 11/2005 | Inoue .......................... 378/97 |

OTHER PUBLICATIONS

Powell G. et al. "Localization of Inter-rib Spaces for Lung Texture Analysis and Computer-aided Diagnosis in Digital Chest Images," Am. Assoc. Phys. Med., vol. 15, No. 4, pp. 581-587 (1988).

* cited by examiner

*Primary Examiner*—Tom Y Lu
(74) *Attorney, Agent, or Firm*—Fitzpatrick, Cella, Harper & Scinto

(57) ABSTRACT

A radiographic image capturing apparatus captures consecutive radiographic images on the basis of the radiation intensity distribution transmitted through a subject, and extracts lung field parts from the captured consecutive radiographic images. A fluctuation condition is detected from the extracted lung field parts, and whether or not the respiratory condition of the subject is suited to radiograph a respiratory behavior of interest is determined on the basis of the detected fluctuation condition.

15 Claims, 7 Drawing Sheets

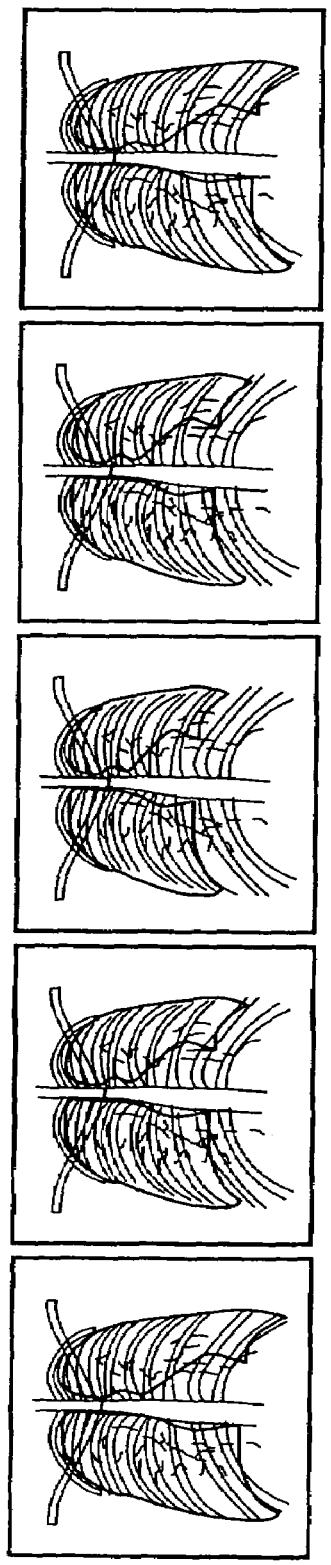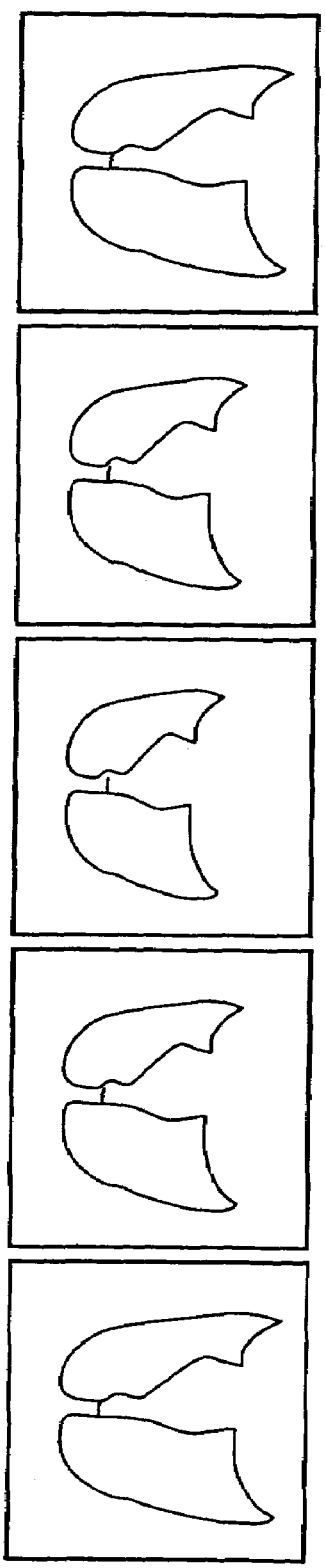
FIG. 2A
FIG. 2B

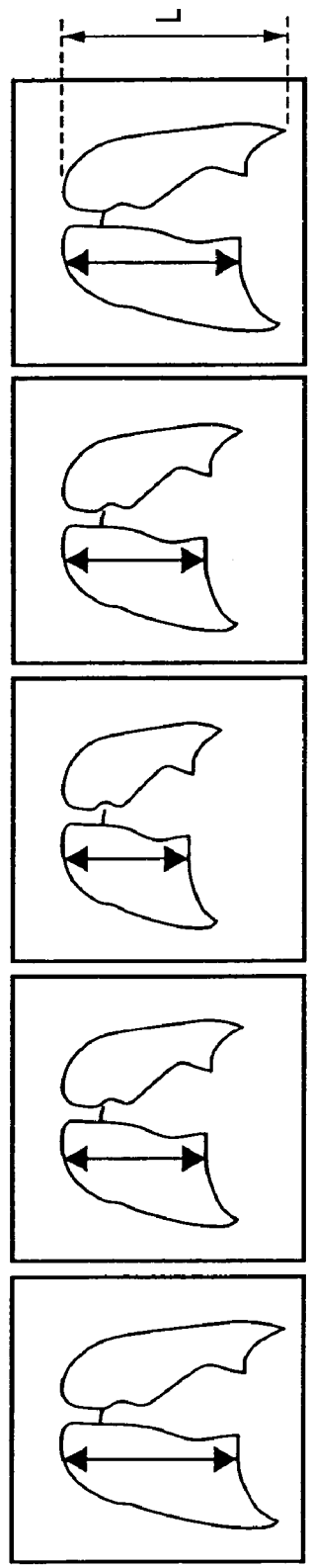
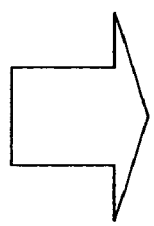
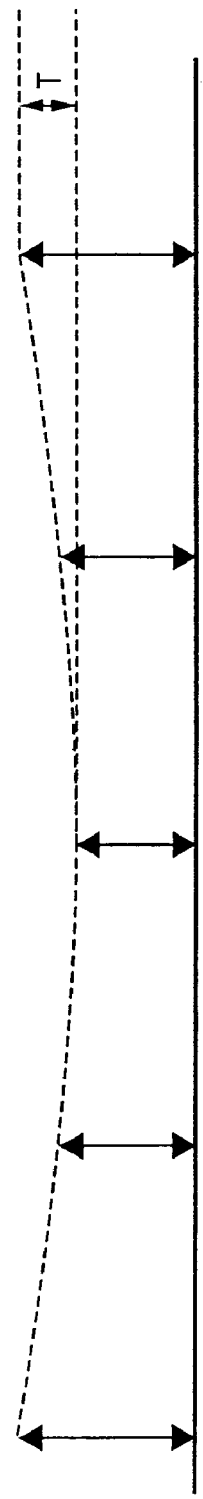
FIG. 3A
FIG. 3B

RADIOGRAPHIC IMAGE CAPTURING APPARATUS

FIELD OF THE INVENTION

The present invention relates to imaging using radiation in the medical field.

BACKGROUND OF THE INVENTION

A technique for imaging a transmission intensity distribution using the material transmission performance of radiation represented by X-rays is a fundamental of modern medical techniques. Since the discovery of X-rays, imaging of the intensity distribution of radiation has adopted a method in which an X-ray intensity distribution is converted into visible light by a phosphor, a latent image is formed by using a silver halide film, and the latent image is developed. In recent years, a method of using a so-called imaging plate has been generally used. This method uses a photostimulable phosphor upon converting an X-ray image into a digital image, and reads out a latent image as an accumulated energy distribution on the photostimulable phosphor by exciting it by a laser beam, thus capturing a digital image. Furthermore, with the advance of semiconductor technologies, a large-sized solid-state image sensing element that can cover the human body size, i.e., a so-called flat panel detector, has been developed, and an X-ray image can be directly converted into a digital image without forming any latent image. In this way, efficient diagnosis can be made.

On the other hand, the behavior of the interior of the human body can itself be observed by imaging fluorescence of weak X-rays using a high-sensitivity image sensing element represented by an image intensifier, and such method is popularly used. The latest flat panel detector has a sensitivity as high as the image intensifier, and allows one to radiograph the behavior of the human body over a broad range.

Chest radiography of the human body is most effective in medical radiography. Since radiographed images over the broad range of the chest, including the abdomen, serve to find many diseases, including lung disease, chest radiography is indispensable in normal health examinations. In recent years, in order efficiently to diagnose chest X-ray images in huge quantities radiographed for the health examination, so-called Computer-Aided Diagnosis (CAD) for applying image analysis to digital chest X-ray images using a computer to help initial diagnosis by a doctor has been put into practical use.

As an example of image analysis, a paper by G. F. Powell, K. Doi, and S. Katsuragawa, "Location of Inter-Rib Spaces for Lung Texture Analysis and Computer-Aided Diagnosis in Digital Chest Images", in *Med. Phys.* 15, 581-587, 1988 (to be referred to as reference 1 hereinafter), describes a technique for extracting a lung field part from a digital chest X-ray mage.

When a suspicion of a disease of some kind is raised by the health examination, a definite diagnosis based on q so-called diagnostic workup is made. Such definite diagnosis normally involves a diagnostic cost several times that of normal radiography, such as a CT/MR scan or the like. Furthermore, the diagnostic workup may often determine that the initial diagnosis is a false diagnosis, and no disease is found. Hence, wasteful use of medical resources has been incurred; this represents part of the reason for medical cost inflation.

In order to avoid such problem, the accuracy of the health examination—the initial diagnosis—must be improved. As a method of improving accuracy while suppressing a rise in cost, it is effective to perform behavior observation by capturing a chest moving image representing the body's behavior in respiration and the like using the aforementioned large-sized flat panel detector. In order to assure stable behavior observation, the patient must breathe in an appropriate fashion. Therefore, imaging must be started while the patient appropriately respires, but it is difficult in practice to recognize and use the correct timing. An apparatus that monitors respiration is available. However, that apparatus is high in cost and involves complicated operations for the patient.

SUMMARY OF THE INVENTION

The present invention has been made in consideration of the aforementioned problems, and has as its object to appropriately capture the behavior of a chest image by a simple operation.

According to one aspect of the present invention, there is provided a radiographic image capturing apparatus comprising: a capturing unit configured to capture consecutive radiographic images on the basis of a radiation intensity distribution transmitted through a subject; an extraction unit configured to extract lung field parts from the consecutive radiographic images captured by the capturing unit; and a determination unit configured to detect a fluctuation condition from the lung field parts extracted by the extraction unit, and determine on the basis of the detected fluctuation condition if a respiratory condition of the subject is suited to radiograph a respiratory behavior.

According to another aspect of the present invention, there is provided a radiographic image capturing method using a radiographic image capturing apparatus which can capture respiratory behavior images, comprising: a capturing step of capturing consecutive radiographic images on the basis of a radiation intensity distribution transmitted through a subject; an extraction step of extracting lung field parts from the consecutive radiographic images captured in the capturing step; and a determination step of detecting a fluctuation condition from the lung field parts extracted in the extraction step, and determining on the basis of the detected fluctuation condition if a respiratory condition of the subject is suited to radiograph a respiratory behavior.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 2A and 2B are views showing extraction of a lung field part;

FIGS. 3A and 3B are views showing an example of extraction of the transitory condition of the lung field part;

DETAILED DESCRIPTION OF THE PREFERRED EMBODIMENTS

Preferred embodiments of the present invention will now be described in detail in accordance with the accompanying drawings.

First Embodiment

In the first embodiment, captured respiratory behavior images are analyzed in real time (parallel to moving image capturing) to detect the transitory condition of the size of a lung field part, and it is checked based on the transitory condition if appropriate respiratory behavior images are obtained. That is, a plurality of images are analyzed while they are captured, and the analysis result (advisability of images) is quickly presented after completion of imaging. If it is determined that images are inappropriate, imaging is prompted again. In the following embodiments, an X-ray image is used as a radiographic image.

Figure 1:
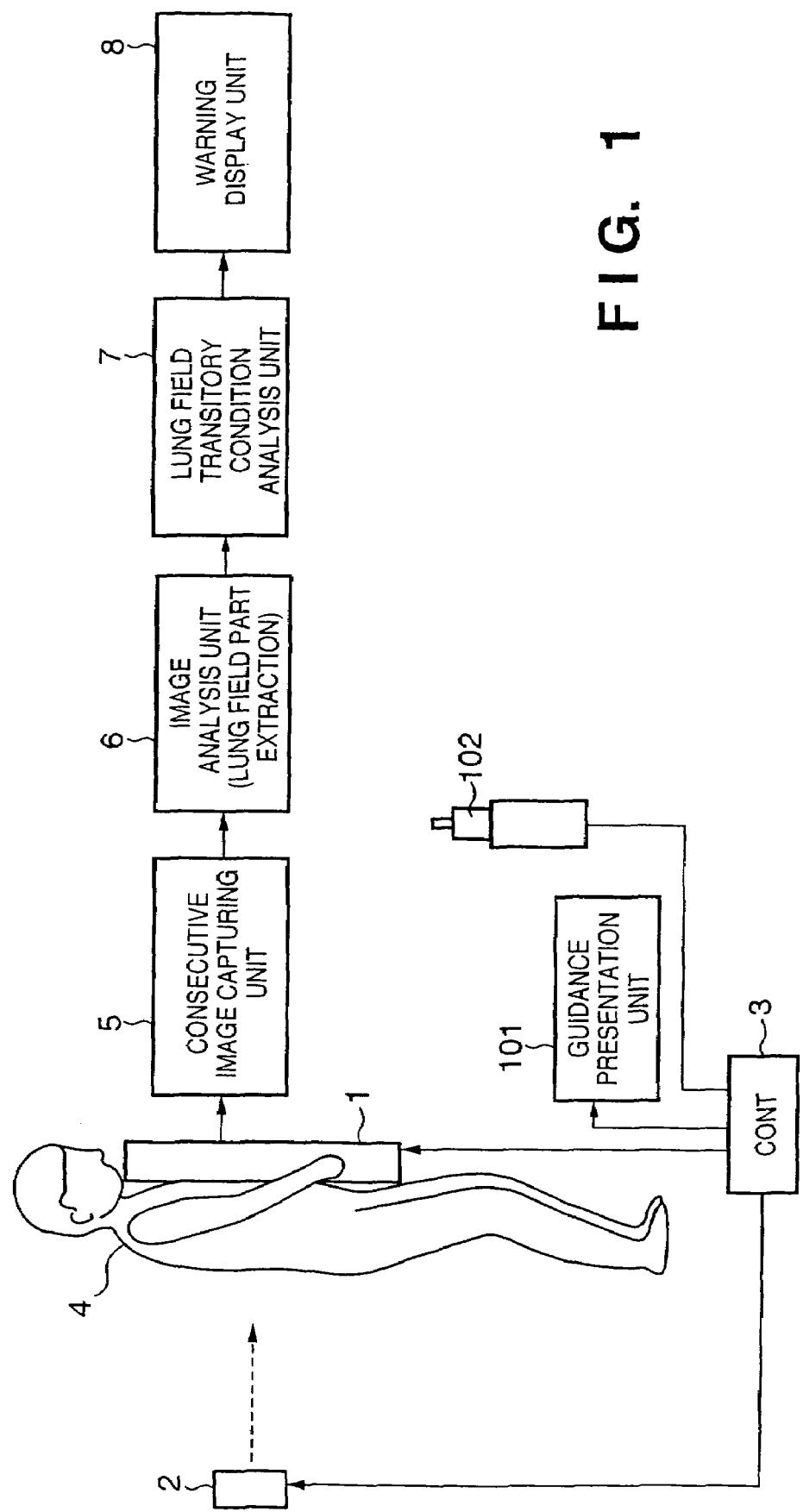
FIG. 1 is a block diagram of the first embodiment of the present invention.

FIG. 1 is a block diagram showing the arrangement of a respiratory behavior imaging apparatus in the first embodiment. Referring to FIG. 1, an X-ray image sensor 1 detects and images the intensity distribution of X-rays which are irradiated from an X-ray generator 2 and reach that sensor. The X-ray image sensor 1 comprises an FPD, and can consecutively capture plural X-ray images. A controller 3 controls the X-ray image sensor 1 and X-ray generator 2 to attain appropriate synchronization between X-ray generation and image capturing. In this embodiment, a human body 4 is the subject. A case will be described below in which the chest is taken as the body part to be imaged. A consecutive image capturing unit 5 captures and saves image data output from the X-ray image sensor 1. An image analysis unit 6 analyzes chest X-ray images captured by the consecutive image capturing unit 5, and extracts lung field parts using a method described in, e.g., reference 1 above. A lung field transitory condition analysis unit 7 calculates the lengths or areas of the lung field parts extracted by the image analysis unit 6 and analyzes the time fluctuation of the lung field parts. When the lung field transitory condition analysis unit 7 determines that the time fluctuation of the lung field parts is inappropriate, a warning display unit 8 generates a warning to the operator and prompts him or her to make re-imaging.

When the chest of the human body 4 consecutively undergoes radiography by the controller 3 while urging a patient to respire, the consecutive image capturing unit 5 captures a plurality of X-ray images representing the respiratory behavior, as shown in FIG. 2A. The image analysis unit 6 extracts, from the chest X-ray images captured, as shown in FIG. 2A, the contours of lung fields, as shown in FIG. 2B, and passes them to the next lung field transitory condition analysis unit 7.

FIGS. 3A and 3B illustrate analysis of the time fluctuation of the lung field parts by the lung field transitory condition analysis unit 7. As shown in FIG. 3A, the length of the lung field is measured from the contour of the lung field, as indicated by the arrow. Note that the length of the lung field is measured at the most upward convex position in the image of the lung field part (a position indicated by the arrow in FIG. 3A). Note that the present invention is not limited to such specific position. For example, the distance between the uppermost and lowermost positions of the lung field part may be measured, as indicated by L in FIG. 3A.

As shown in FIG. 3B, the measured lengths are time-serially arranged to form a graph, and their fluctuation is analyzed. The analysis is done by checking a fluctuation amount T of the lung field lengths or the curved pattern of the graph. For example, if T is smaller than a given prescribed value, the patient is unlikely to breathe in the desired way during this time, or images for one cycle of respiration are unlikely to be radiographed. Hence, a warning is immediately generated to prompt re-imaging. If the curved pattern of the graph gets distorted (e.g., the difference between the neighboring "lengths" changes extremely), it is determined that the respiratory behavior is inappropriate. Hence, a warning is immediately generated to prompt re-imaging. In this embodiment, the lung field lengths are measured. Alternatively, any other parameters such as lung field areas and the like may be used as long as they can indicate the respiratory behavior.

Note that a guidance presentation unit 101 may present guidance that indicates an appropriate respiration pace to the patient before radiographing the behavior images. As an example of such guidance, proper respiratory timing may be indicated by tone pitches. In this case, the guidance preferably makes the patient inhale when the tone pitch becomes higher, and exhale when the tone pitch becomes lower. In general, when the tone frequency becomes high, a person normally has an image of stretching a body, and can easily create an image when he or she inhales. The tone to be generated may be a mechanical tone having a single frequency, mixed tones like a so-called chord, or a tone generated by an instrument such as a piano or the like. However, it is important to shift the frequency up and down as a whole, as described above.

As an example of such respiration guidance, a display that instructs actions of respiration may be displayed on a display unit which is arranged at a position where the patient can see it. For example, an animation or the like is displayed in tune with respiration, thus specifying a respiratory rhythm to the patient.

Such audible or visible respiration guidance is made in a "practice mode" without generating any X-rays. By repeating respiratory actions several times in accordance with the guidance, the patient can master the appropriate respiration for imaging within a short period of time. The mentioned audible and visible types of respiration guidance have been exemplified, but any other types of guidance may be adopted. For example, the force of a slight breeze in the patient's face, a vibrator, and the like may be similarly used as a respiration guidance. Also, an aromatic odor may be mixed in a slight breeze to urge smoother respiratory actions. Furthermore, a plurality of different guidances (e.g., audible and visual guidances) may be combined.

The operator performs imaging by actually radiating X-rays, in an "imaging mode". At this time, the same respiration guidance as in the practice mode is presented to the patient. The operator does not start X-ray irradiation in the initial, or indeed for several, respiration cycles, and waits to operate a radiation button 102 to start X-ray irradiation until the patient has gotten into the appropriate respiration rhythm. In this way, X-ray images for one cycle of appropriate respiratory actions are captured. Note that the controller 3 executes X-ray irradiation in synchronism with the respiration rhythm indicated by the guidance provided by the guidance presentation unit 101 after the radiation instruction is input by the radiation button 102. For example, the controller 3 controls to start X-ray irradiation at a transition timing from inhalation to exhalation.

Figure 6:
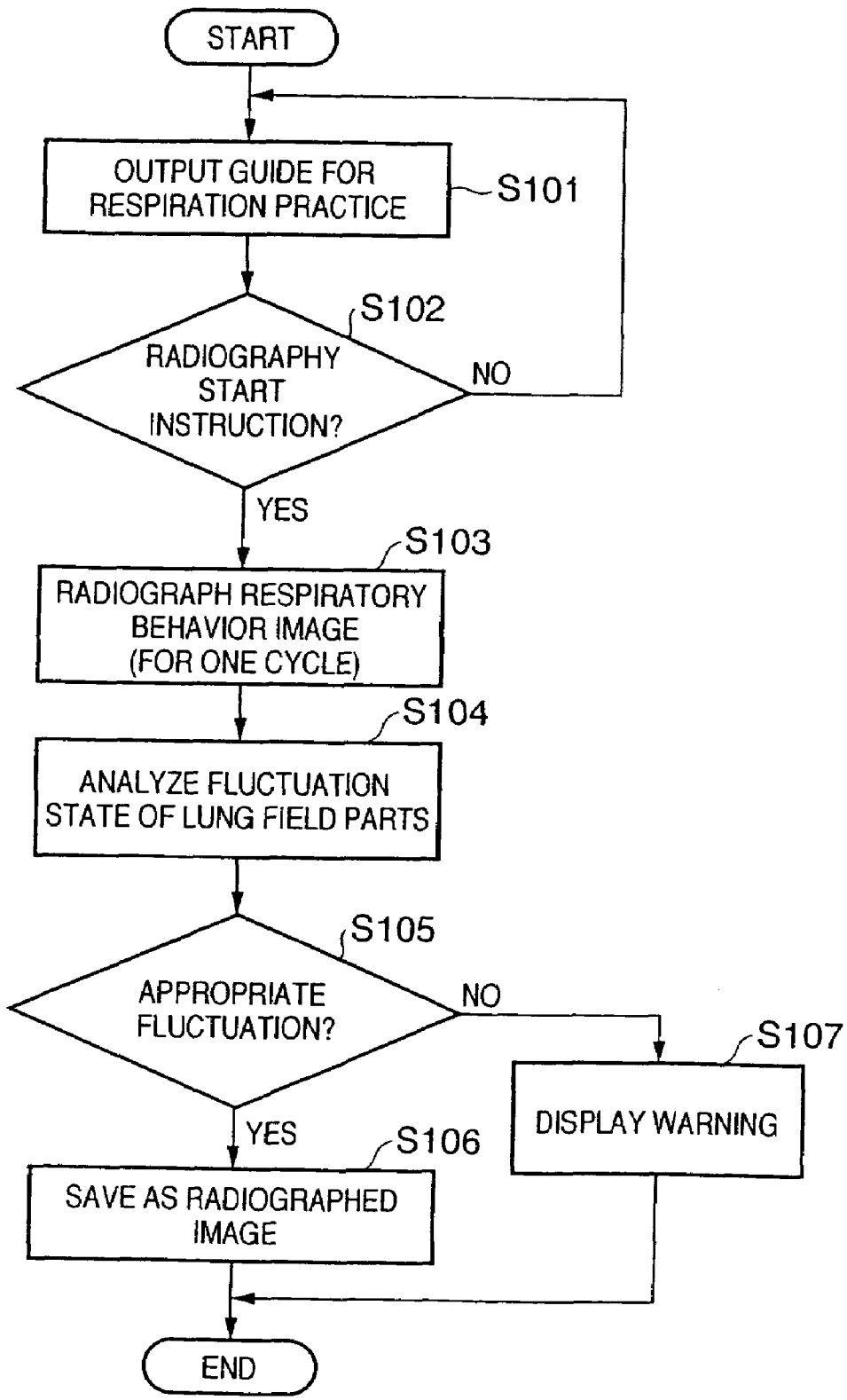
FIG. 6 is a flowchart for explaining an imaging process of a respiratory behavior image according to the first embodiment.

The aforementioned operation will be described below with reference to the flowchart shown in FIG. 6. As described above, a guidance for appropriate respiration is presented to the user to make him or her breathe (step S101). If the operator inputs an X-ray imaging start instruction to the controller 3 at an appropriate timing, the consecutive image capturing unit 5 presents the respiration guidance to make the patient respire several times, and then executes X-ray imaging (steps S102 and S103). In this X-ray imaging, respiratory behavior images for one cycle are radiographed. The duration of one cycle (imaging time) is preferably set to be equal to that assumed by the respiration guidance.

After the respiratory behavior images are captured, the image analysis unit 6 extracts lung field parts, and the lung field transitory condition analysis unit 7 determines the suitability of the respiratory behavior images on the basis of the time fluctuation of the lung field parts (step S104). If appropriate respiration is determined to have occurred, the behavior images are saved as the imaging results or are output onto films or the like (step S106). On the other hand, if an inappropriate respiration condition is determined to have occurred during the radiography, a message that advises accordingly is displayed, and re-imaging is prompted (step S107).

As described above, according to the first embodiment, since the respiration condition of the captured respiratory behavior images is automatically determined, images in the inappropriate respiration condition can be prevented from being output for diagnosis.

Second Embodiment

In the first embodiment, the respiration condition of images radiographed as respiratory behavior images is checked. In the second embodiment, after a respiration action is instructed to the patient, size variations of a lung field part are detected from images captured by weak X-ray irradiation, a timing of appropriate respiration is automatically detected, and imaging starts or is instructed to start at that timing.

Figure 4:
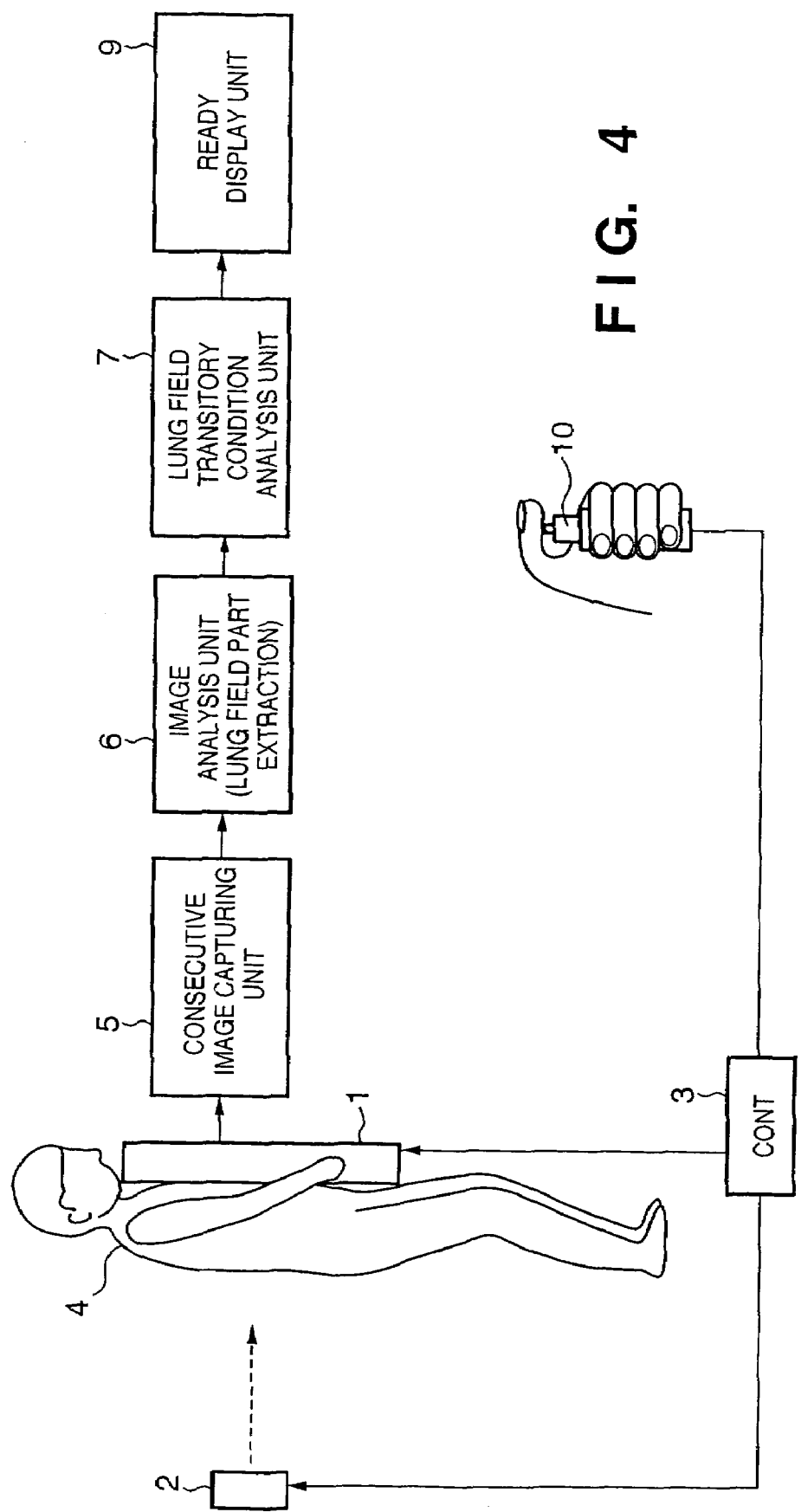
FIG. 4 is a block diagram of the second embodiment of the present invention.

FIG. 4 is a block diagram showing the arrangement of a respiratory behavior imaging apparatus according to the second embodiment. The same reference numerals in FIG. 4 denote the same parts as those in the first embodiment (FIG. 1). A ready display unit 9 is a display device which indicates that the patient keeps appropriate respiration, and makes a so-called ready display indicating that the subject is ready for imaging. An X-ray irradiation button 10 is a switch used to issue an X-ray irradiation start instruction for imaging. Note that the X-ray generator 2 of the second embodiment has an arrangement that can continuously generate very weak X-rays.

The operator urges the patient to breathe continuously. At this time, by operating an operation switch or the like (not shown), the X-ray generator 2 continuously generates X-rays as weak as the image analysis unit 6 can use in its process of extracting lung field parts. In other words, even unclear images of weak X-rays allow the image analysis unit 6 to execute the process for extracting lung field parts.

Figure 5:
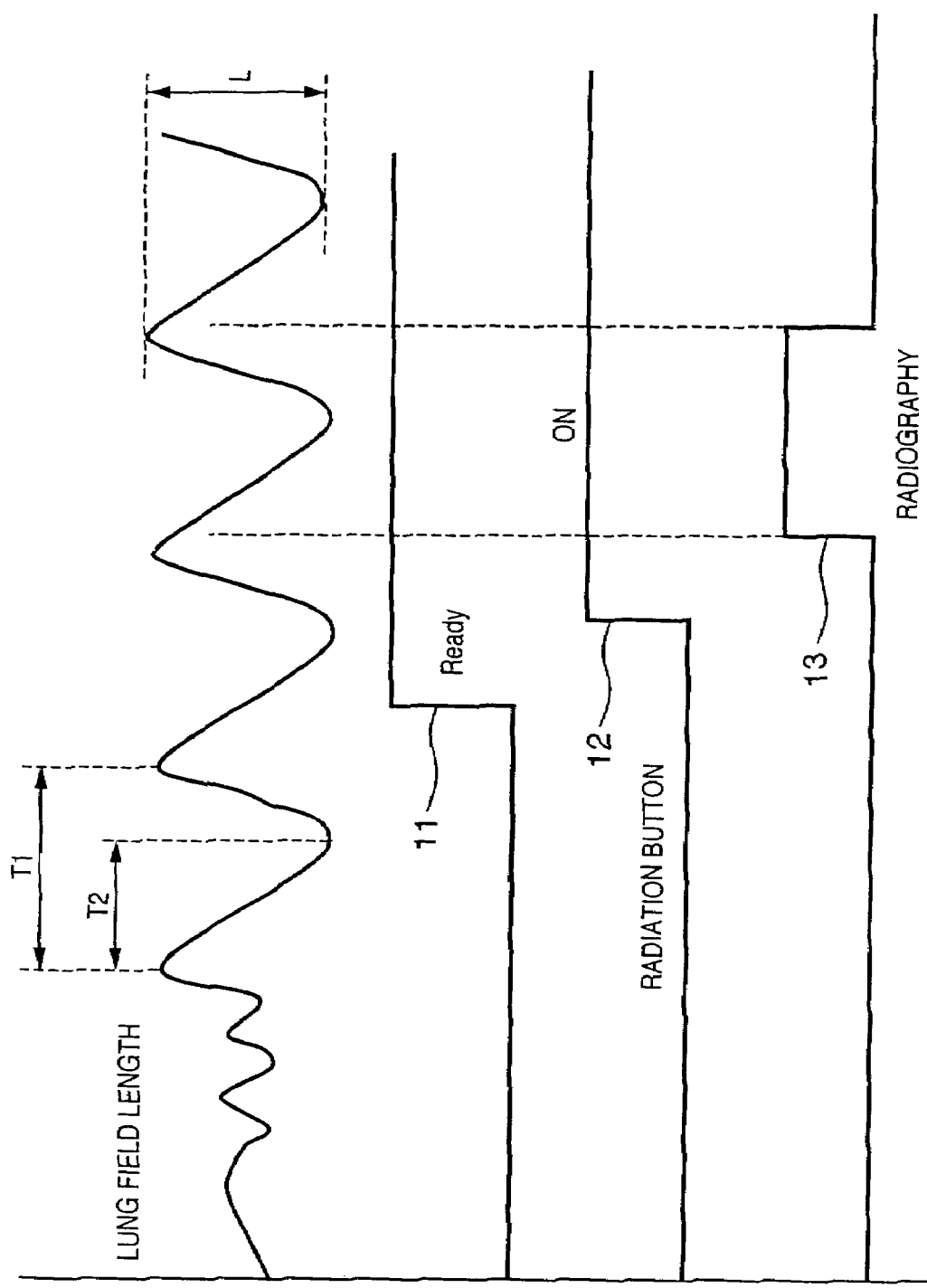
FIGS. 5A to 5D are timing charts showing the imaging mode of the second embodiment.

FIGS. 5A to 5D are timing charts indicating the operation timings of the respiratory behavior imaging process according to the second embodiment. The lung field transitory condition analysis unit 7 outputs and analyzes the fluctuation of the lung field lengths, as shown in FIG. 5A. Note that detection of the fluctuation of the lung field lengths is performed as has been explained above with reference to FIGS. 2 and 3. Note that the suitability of the patient's breathing can be determined by various methods. For example, in this embodiment, it is determined that an appropriate respiratory condition is obtained when a time interval (T1) between the neighboring peaks on the maximum side of the lung field lengths, a time interval (T2) between the neighboring maximum and minimum peaks, and a fluctuation (L) in the graph shown in FIG. 5A fall within a predetermined range for a predetermined period.

The ready display unit 9 makes an imaging ready display at a timing 11 at which it can be determined that the lung field motion becomes appropriate. (FIG. 5B). The operator presses the radiation button 10 after he or she confirms this ready display (12 in FIG. 5C). Even after depression of the radiation button, the lung field length analysis is continued to determine an appropriate imaging range, and the respiratory behavior in a section 13 in FIG. 5D is radiographed (FIG. 5D).

Figure 7:
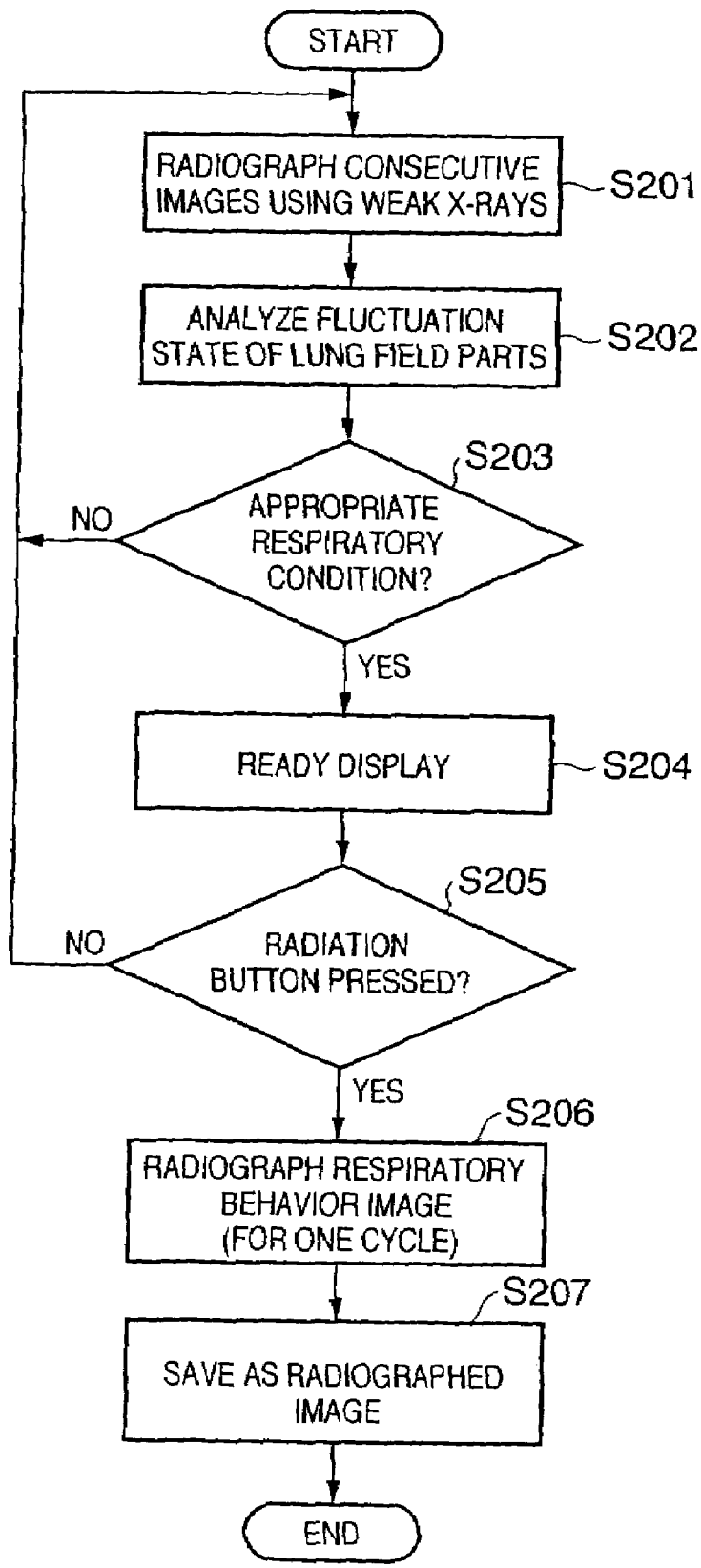
FIG. 7 is a flowchart for explaining an imaging process of a respiratory behavior image according to the second embodiment.

The aforementioned operation of the second embodiment will be described below with reference to the flowchart of FIG. 7.

Imaging of consecutive images using weak X-rays is started by a predetermined operation (step S201). The consecutive image capturing unit 5 consecutively captures X-ray images of weak X-rays and sends them to the image analysis unit 6. The image analysis unit 6 extracts the contours of a lung field from the consecutive X-ray images, and the lung field transitory condition analysis unit 7 analyzes the fluctuation of the extracted lung field lengths (step S202). With this analysis, whether or not the fluctuation of the lung field becomes respiration suited to radiograph a respiratory behavior is checked (step S203). If appropriate respiration is determined, the ready display unit 9 notifies the operator of that message. With this ready display, the operator can input an imaging start instruction of a respiratory behavior using the radiation button 10 at an appropriate timing.

After that, upon depression of the radiation button, X-ray images of weak X-rays are continuously analyzed, an appropriate imaging timing is detected, and radiography of the respiratory behavior is executed (step S206). In this embodiment, a period from a timing at which the lung field length becomes maximum to the next maximum timing is detected (estimated) on the basis of the aforementioned transitory condition analysis, and the respiratory behavior is radiographed to have this period as one cycle.

In this embodiment, radiation starts when the operator presses the radiation button 10 after he or she confirms a ready state by means of ready display. However, imaging may be started if the ready state is displayed without using the radiation button.

As described above, according to the second embodiment, since imaging of the respiratory behavior starts after an appropriate respiratory condition is detected based on X-ray images of weak X-rays, it becomes more likely to radiograph appropriate respiratory behavior images by single imaging. More specifically, appropriate respiratory behavior images can be radiographed with a smaller X-ray dose.

After the respiratory behavior images are radiographed in step S206 of the second embodiment, the fluctuation condition of the lung field may also be analyzed to check if appropriate images are radiographed. That is, after the process in step S206, the processes in steps S104 to S107 of the first embodiment may be executed.

As described above, according to the above embodiments, since the advisability of the respiratory conditions of respiratory behavior images is automatically determined, an appropriate imaging result in behavior imaging of a chest image can be easily obtained.

As many apparently widely different embodiments of the present invention can be made without departing from the spirit and scope thereof, it is to be understood that the invention is not limited to the specific embodiments thereof except as defined in the claims.

CLAIM OF PRIORITY

This application claims priority from Japanese Patent Application No. 2004-136018, filed on Apr. 30, 2004, which is hereby incorporated by reference herein.

What is claimed is:

1. A radiographic image capturing apparatus comprising:
   a capturing unit configured to capture consecutive radiographic images on the basis of a radiation intensity distribution transmitted through a subject;
   an extraction unit configured to extract lung field parts from the consecutive radiographic images captured by said capturing unit; and
   a determination unit configured to detect a fluctuation condition from the lung field parts extracted by said extraction unit, and determine on the basis of the detected fluctuation condition if a respiratory condition of the subject is suited to radiograph a respiratory behavior.

2. The apparatus according to claim 1, further comprising:
   a presentation unit configured to present a respiratory pace, wherein radiography of the respiratory behavior is executed by causing said capturing unit to function in synchronism with the respiratory pace presented by said presentation unit.

3. The apparatus according to claim 1, further comprising:
   a notification unit configured to, when said determination unit determines that the respiratory condition is inappropriate, issue a message that advises accordingly after the end of radiography.

4. The apparatus according to claim 1, wherein the processes of said extraction unit and said determination unit are executed in parallel with the capturing operation of consecutive images by said capturing unit.

5. The apparatus according to claim 1, further comprising:
   a control unit configured to capture consecutive radiographic images using radiation weaker than a dose used to radiograph diagnostic images prior to radiography of the respiratory behavior,
   to extract lung field parts from the captured consecutive radiographic images, and
   to issue, when it is determined based on a fluctuation state detected from the extracted lung field parts that a respiratory condition of the subject is suited to radiograph a respiratory behavior, a message that advises accordingly.

6. The apparatus according to claim 1, further comprising:
   a control unit configured to capture consecutive radiographic images using radiation weaker than a dose used to radiograph diagnostic images prior to radiography of the respiratory behavior,
   to extract lung field parts from the captured consecutive radiographic images, and
   to start, when it is determined based on a fluctuation state detected from the extracted lung field parts that a respiratory condition of the subject is suited to radiograph a respiratory behavior, radiography of diagnostic images by said capturing unit.

7. The apparatus according to claim 6, wherein said control unit determines a radiography start timing and radiography time of the respiratory behavior on the basis of the fluctuation state detected from the lung field parts.

8. The apparatus according to claim 1, wherein said determination unit determines based on a fluctuation of lengths of the extracted lung field parts whether or not the respiratory condition of the subject is suited to radiograph the respiratory behavior.

9. The apparatus according to claim 1, wherein said determination unit determines based on a fluctuation of areas of the extracted lung field parts whether or not the respiratory condition of the subject is suited to radiograph the respiratory behavior.

10. The apparatus according to claim 1, wherein said determination unit detects the fluctuation condition by analyzing a fluctuation of sizes of the lung field parts upon respiration.

11. A radiographic image capturing apparatus comprising:
    a capturing unit configured to capture consecutive radiographic images using radiation weaker than a dose used to radiograph diagnostic images prior to radiography of a respiratory behavior;
    an extraction unit configured to extract lung field parts from the consecutive radiographic images captured by said capturing unit; and
    a determination unit configured to determine based on a fluctuation state detected from the lung field parts extracted by said extraction unit whether or not a respiratory condition of a subject is suited to start radiography of a respiratory behavior.

12. The apparatus according to claim 11, further comprising:
    an instruction unit configured to, when said determination unit determines that the respiratory condition of the subject is suited to start radiography, issue a radiography start instruction of diagnostic images.

13. The apparatus according to claim 11, further comprising:
    an execution unit configured to, when said determination unit determines that the respiratory condition of the subject is suited to start radiography, start radiography of diagnostic images by said capturing unit.

14. A radiographic image capturing method using a radiographic image capturing apparatus which can capture respiratory behavior images, comprising:
    a capturing step of capturing consecutive radiographic images on the basis of a radiation intensity distribution transmitted through a subject by use of said radiographic image capturing apparatus;
    an extraction step of extracting lung field parts from the consecutive radiographic images captured in the capturing step by use of said radiographic image capturing apparatus; and
    a determination step of detecting a fluctuation condition from the lung field parts extracted in the extraction step, and determining on the basis of the detected fluctuation condition if a respiratory condition of the subject is suited to radiograph a respiratory behavior by use of said radiographic image capturing apparatus.

15. A radiographic image capturing method using a radiographic image capturing apparatus which can capture respiratory behavior images, comprising:
    a capturing step of capturing consecutive radiographic images using radiation weaker than a dose used to radiograph diagnostic images prior to radiography of a respiratory behavior by use of said radiographic image capturing apparatus;
    an extraction step of extracting lung field parts from the consecutive radiographic images captured in the capturing step by use of said radiographic image capturing apparatus; and
    a determination step of determining based on a fluctuation state detected from the lung field parts extracted in the extraction step whether or not a respiratory condition of a subject is suited to start radiography of a respiratory behavior by use of said radiographic image capturing apparatus.

* * * * *